(12) United States Patent
Wilson et al.

(10) Patent No.: US 7,829,755 B2
(45) Date of Patent: Nov. 9, 2010

(54) SYSTEM AND METHOD FOR TREATING INFECTIOUS WASTE MATTER

(75) Inventors: Joseph H. Wilson, Danville, IN (US); Gordon I. Kaye, Troy, NY (US); Robert L. Hahn, Brownsburg, IN (US); Peter B. Weber, Delmar, NY (US); Kevin A. Morris, Avon, IN (US)

(73) Assignee: Digestor, LLC, Brownsburg, IN (US)

( * ) Notice: Subject to any disclaimer, the term of this patent is extended or adjusted under 35 U.S.C. 154(b) by 105 days.

(21) Appl. No.: 12/364,012

(22) Filed: Feb. 2, 2009

(65) Prior Publication Data

US 2009/0137858 A1 May 28, 2009

Related U.S. Application Data

(63) Continuation of application No. 11/457,297, filed on Jul. 13, 2006, now abandoned, which is a continuation of application No. 10/201,121, filed on Jul. 23, 2002, now Pat. No. 7,183,453, which is a continuation of application No. PCT/US01/02319, filed on Jan. 24, 2001, application No. 12/364,012, which is a continuation of application No. 10/263,043, filed on Oct. 2, 2002, now abandoned, which is a continuation-in-part of application No. 09/171,447, filed as application No. PCT/US97/06616 on Apr. 21, 1997, now Pat. No. 6,472,580.

(60) Provisional application No. 60/178,051, filed on Jan. 24, 2000, provisional application No. 60/036,665, filed on Apr. 22, 1996.

(51) Int. Cl.
*A62D 3/37* (2007.01)

(52) U.S. Cl. ...................................... 588/319; 588/405

(58) Field of Classification Search ................. 588/313, 588/321, 316, 317, 319, 405, 411
See application file for complete search history.

*Primary Examiner*—Edward M Johnson
(74) *Attorney, Agent, or Firm*—Woodard Emhardt Moriarty McNett & Henry

(57) ABSTRACT

A system and method is provided for producing a safely disposable end product from waste matter containing undesirable materials, such as infectious, biohazardous, hazardous, or radioactive elements. The method comprises the steps of providing a highly alkaline solvent, immersing the waste matter containing the undesirable materials within the highly alkaline solvent, and heating the solvent. The waste matter containing the undesirable materials is allowed to remain within the solvent until digested, thereby forming a solution void of any infectious or biohazardous elements and/or containing a decreased concentration of radioisotope.

18 Claims, 6 Drawing Sheets

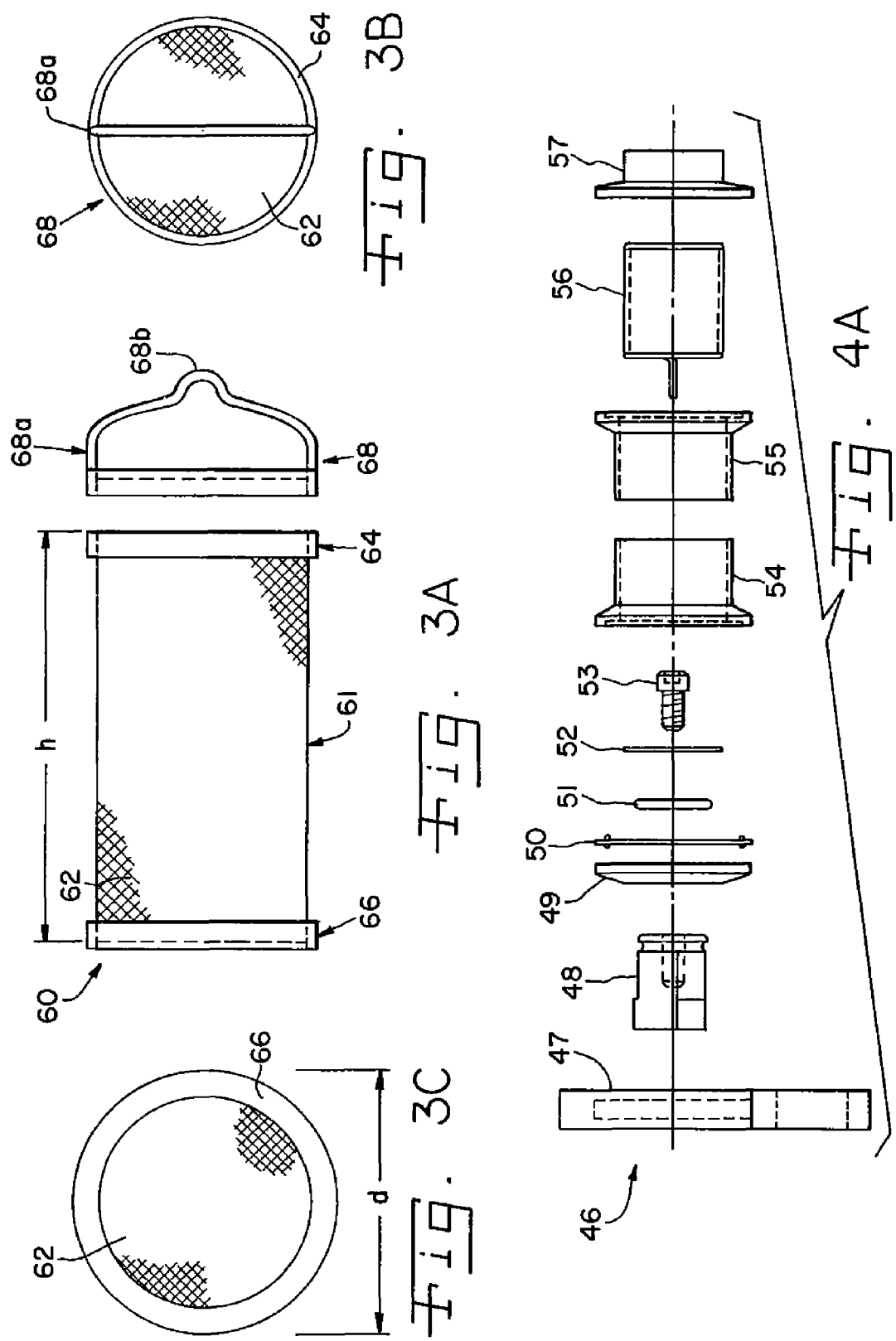

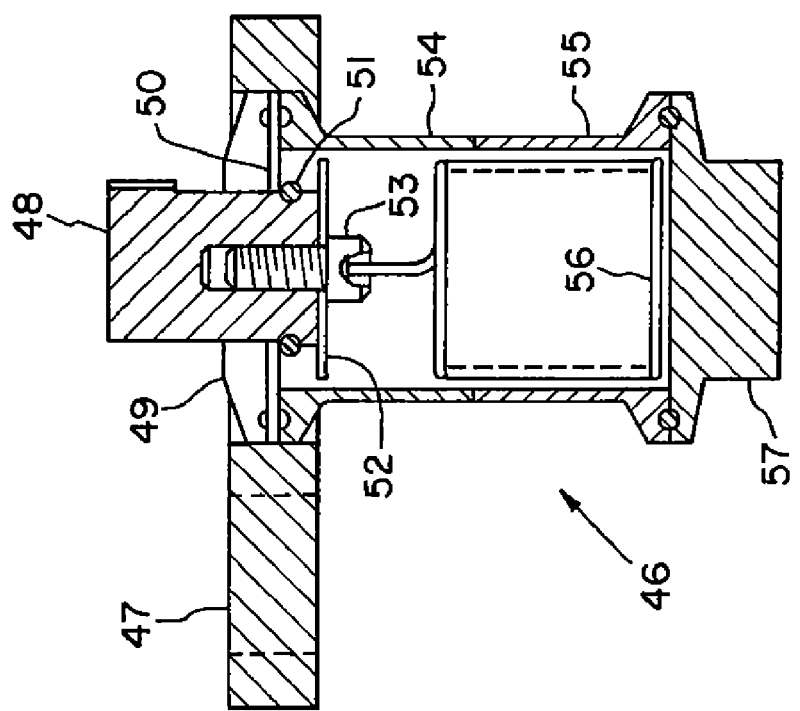
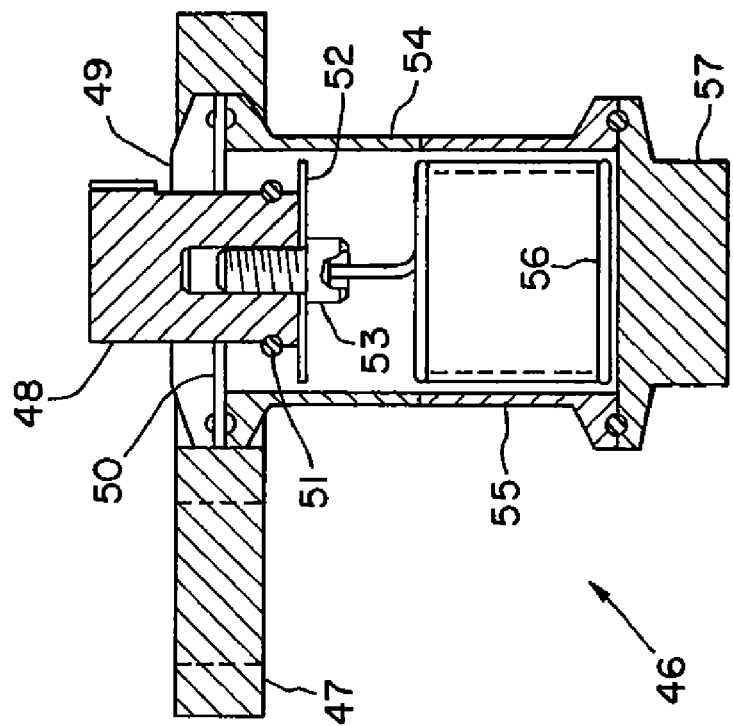
Fig. 4B OPEN
Fig. 4C CLOSED

SYSTEM AND METHOD FOR TREATING INFECTIOUS WASTE MATTER

CROSS REFERENCE TO RELATED APPLICATIONS

This application is a continuation of Ser. No. 11/457,297 filed Jul. 13, 2006, now abandoned which is a continuation of Ser. No. 10/201,121, filed Jul. 23, 2002, now U.S. Pat. No. 7,183,453 which is a continuation of PCT/US01/02319, filed Jan. 24, 2001, which claims the benefit of 60/178,051, filed Jan. 24, 2000. This application is also a continuation of Ser. No. 10/263,043, filed Oct. 2, 2002, now abandoned which is a continuation-in-part of Ser. No. 09/171,447, filed Oct. 20, 1998, now U.S. Pat. No. 6,472,580 which is the 371 national stage of PCT/US97/06616, filed Apr. 21, 1997, which claims the benefit of 60/036,665, filed Apr. 22, 1996. The disclosure of Ser. No. 09/171,447, now U.S. Pat. No. 6,472,580, titled "Methods for Treatment and Disposal of Regulated Medical Waste," is incorporated herein by reference.

FIELD OF THE INVENTION

This invention relates to the field of waste disposal and, more particularly, to a system and method for the digestion and sanitary disposal of infectious waste material and other biohazardous or radioactive waste.

BACKGROUND OF THE ART

Many facilities, such as hospitals, various health-care facilities, research and teaching institutions, food preparation facilities, and the like, produce considerable amounts of infectious, biohazardous, or radioactive waste. Such waste may include surgical and pathological tissues, animal tissues, cadavers, blood and other bodily fluids, disposable matter exposed to blood, and other potentially infectious or dangerous body fluids of patients or animals. Such waste is classified in the United States as "regulated medical waste" (RMW) under state regulations, and must be disposed of in strict compliance with the applicable governmental regulations.

Health-related organizations and governmental regulatory agencies have become increasingly concerned with the adequacy of existing cleaning and disposal methods. It has been discovered that some potentially biohazardous agents, such as prokaryotes, or infective proteins (prions) do in fact survive standard autoclaving procedures. Thus, more effective sterilization techniques have been sought for treating solid infectious biomedical waste and aqueous solutions containing such waste.

In addition, universities and other research facilities likewise produce significant amounts of such waste. For example, in conducting experiments in cell lines, tissues, or animals, it is common to introduce dyes, toxic chemicals, or infectious agents into the test subject. Moreover, radioactive materials are also commonly used as a tool to enhance chemical, biochemical, pharmaceutical, biomedical, and biological research. It is common to label drugs or chemical compounds with radioisotopes in order to study efficiently and accurately where these compounds are metabolized and incorporated within the body. After completion of the test and analysis, due to the introduction of infectious agents or hazardous or radioactive material into the tissue, the remaining tissue or animal carcass may fall under the classification of "regulated medical waste," hazardous waste, or low-level radioactive waste ("LLRW"). In addition, animal waste, animal bedding, handling materials, and other matter exposed to any animal body fluids or excretions may also need to be treated as infectious or hazardous waste material, thus requiring disposal in accordance with the applicable governmental regulations.

Moreover, it is common today for health care organizations to clean material, instruments or surface areas exposed to infectious agents, including zoonotic agents, with disinfectants such as formaldehyde or glutaraldehyde. Spent cleaning solution is considered hazardous liquid waste and must also be disposed of in compliance with governmental regulations. The cost of disposing of such waste, on an institutional basis, can be quite high. Further, formaldehyde, glutaraldehyde, phenols and like materials, are commonly used for embalming tissues and in fixation of infectious biological materials. Thus, these tissues and the fixative agents may also have to be disposed of as "regulated medical waste," hazardous waste, or mixed waste in compliance with the applicable governmental regulations.

Further, animal carcasses containing compounds labeled with $^{14}C$ or $^{3}H$ or other radioisotopes are classified as LLRW. Because state and federal guidelines regulate the disposal of LLRW, special precautions must be followed in their disposal. Currently, the two methods commonly used in disposing of this type of waste are incineration and land burial. Presently, federal law allows for incineration only when the animal carcass contains a radioisotope concentration below a certain level. However, even when radioisotope concentrations are below this level, incineration may be further limited by state and local agencies. When the levels of radioactivity in the animal carcasses are below acceptable de minimis levels as defined by federal, state, and local authorities, the disposal thereof is not subject to any additional regulation as a radioactive waste. However, to further complicate matters, the incineration of radioactive animal carcasses at any level is prohibited in certain major metropolitan areas. Nonetheless, the general process of incineration itself, even when no radioactive materials are involved, is subject to additional regulations, such as those requiring licensing from a state or local environmental agency. Additionally, future increases in the requirements for incinerator designs and function under clean air regulations put in doubt the continued availability of incineration as a practical method for disposing of animal carcasses classified as LLRW or for any non-radioactive carcasses or human pathological waste.

Presently, the only real alternative to incineration for radioactive animal carcasses is burying the carcasses in a licensed LLRW disposal facility. This method entails the packing of the entire carcasses in lime and adsorbents, repacking them in special drums and shipping the drums to a LLRW site. Currently there are only two such sites in the United States, located at Hanford, Wash., and Banwell, S.C. Due to the limited number of land burial sites currently operating in the United States, it is extremely costly to dispose of any radioactive waste by this method; it is disproportionately costly for animal carcasses containing low level radioactive waste due to the size and weight of the carcass. Due to the extremely high cost associated with land burial and the limitations on access to current sites, the feasibility of land burial as a method of disposing of animal carcasses classified as LLRW remains in doubt.

It is known in the art that low levels of certain radioactive waste may be disposed of to a sanitary sewer under federal regulations with appropriate record keeping and/or monitoring. This includes isotopes in aqueous solution at levels below the maximum permissible concentration (MPC) as defined by 10 C.F.R. 20 and radioisotopes in human waste. Such a procedure has been utilized, for example, in the disposal of radioactive waste generated by many patients undergoing treatments for cancer. Today, a common method of treating cancer is by radiation therapy, which often involves the absorption of radioactive compounds. Many of these radioactive compounds eventually leave the body through fecal and urinary excretions. These excretions will contain small amounts of radioactive material. However, this radioactive material is disposed of through the general sewage system because the level of the radioactive materials discharged by the body into the sewer system is sufficiently diluted such that it no longer poses any hazard to public health and safety. This process is well within the state and federal disposal regulations for LLRW disposal. However, LLRW contained in animal remains are not readily capable of disposal through such means because the animals are naturally solid waste.

It is also known in the art that substances containing keratin, such as hair and nails, may be dissolved by means of acid or alkaline hydrolysis, as disclosed in U.S. Pat. No. 1,974,554 issued to Ziegler. It is further known that hydrolysis of proteins containing keratin may be carried out with alkaline solvents. It is even further disclosed in U.S. Pat. No. 5,332,532 to Drs. Kaye and Weber, which patent is commonly owned by the assignee of the present application, that such hydrolysis may be utilized on proteins contaminated with radioactive materials.

Of the known methods of disposing of infectious, biohazardous, or low-level radioactive waste, each faces an indeterminable future under the ever-changing breadth of the environmental laws. Furthermore, each is extremely costly, putting an unneeded drain on already strained research and waste management budgets of hospitals, universities and other institutions. Thus, a need persists for means of safely and inexpensively treating waste matter containing infectious, biohazardous, or radioactive materials, and for the safe and convenient disposal of the resultant aqueous and solid waste materials.

SUMMARY OF INVENTION

This need is satisfied and the limitations and expenses of the prior art are overcome, in accordance with the principles of the present invention, by providing a system and method for producing a safely disposable solution and solid waste from infectious or biohazardous human or animal tissue, regulated medical waste, or any other material containing undesirable elements. This invention provides a system for producing a safely disposable sterile solution and sterile solid waste, comprising a sealable tank or vessel capable of containing a highly basic solvent therein, heating means for heating the highly basic solvent, filtering means, means for removing the odor created by such activities, means for removing the post-digestion resultant aqueous solution and any solid waste from within the vessel, and means for disposing of the resultant aqueous and/or solid waste via conventional means.

The method provided by the invention generally comprises the steps of providing a sealable vessel, filling the vessel with a highly basic solvent, immersing the waste matter containing the undesirable elements within the highly basic solvent, and heating the highly basic solvent. The waste matter is allowed to remain within the highly basic solvent until the hydrolyzable matter is digested, thereby forming a sterile solution and sterile solid waste. The aqueous solution and any resultant solid waste may then be disposed of through conventional means, such as a sanitary sewer or local landfill facility.

In another aspect of the invention, hazardous materials may be removed from the digest and separately disposed of in an appropriate manner, such as a specially designated landfill or an incineration facility. Paraffin or wax may be added to the RMW prior to or subsequent to the digestion cycle. Upon heating the materials, the paraffin or wax melts and becomes distributed through the aqueous solution. After the waste has been digested and the aqueous solution allowed to cool, the lipid-like materials separate out from and float to the surface of the solution where they re-solidify upon cooling to room temperature. Lipid soluble waste materials may then be removed from the aqueous phase upon separation of the lipid phase because they have become incorporated within the lipid phase. Thus, removing the lipid phase from the solution effectively removes lipid soluble hazardous materials not degraded or otherwise consumed in the alkaline treatment as well.

As used herein, "regulated medical waste" shall mean any waste potentially containing infectious agents that can cause infection in humans or animals. Such regulated medical waste includes but is not limited to tissues (human or animal), cloth, plastic, paper, animal carcasses, bedding and other matter potentially containing infectious or biohazardous agents.

Accordingly, it is an object of this invention to provide a system and method for safely treating and disposing of waste matter containing undesirable elements, such as infectious, biohazardous, hazardous, or radioactive elements or agents.

BRIEF DESCRIPTION OF THE DRAWINGS

FIGS. 3A, 3B and 3C are side, top and bottom elevations, respectively, of a holding container for receiving and storing the waste matter within the vessel chamber interior during the digestion cycle;

FIG. 4A shows an exploded elevation of a unique vacuum balancer device provided by the invention;

FIGS. 4B and 4C show the vacuum balancer of FIG. 4A in its open and closed states, respectively.

BEST MODE FOR CARRYING OUT THE INVENTION

Figure 1:
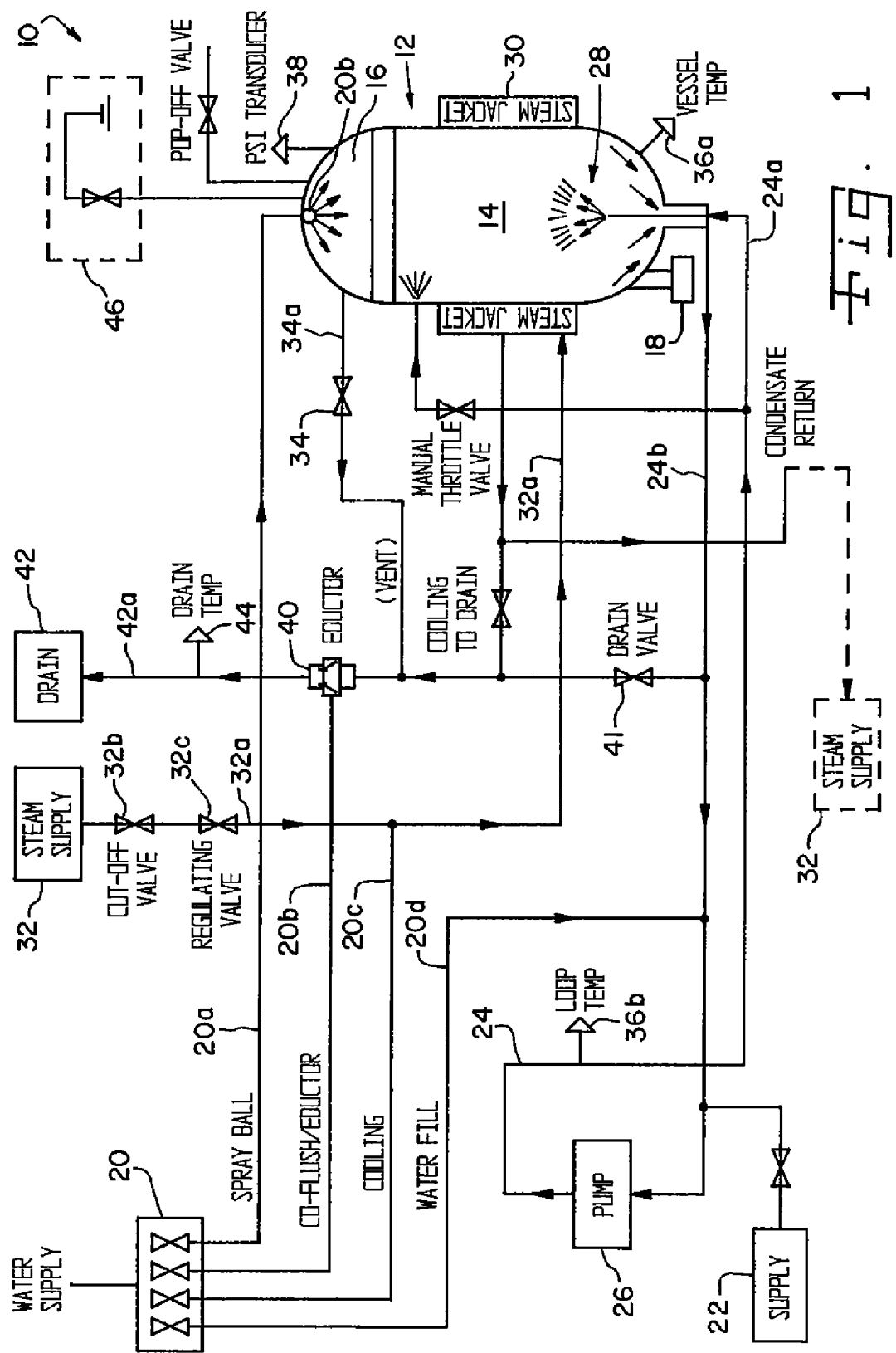
FIG. 1 is a schematic representation of the system provided by a currently preferred embodiment of the invention.

This invention involves a system and method for treating and safely disposing of waste matter containing undesirable agents or elements, such as but not limited to infectious, biohazardous, hazardous, and radioactive materials. The system and method of this invention is designed and intended to comply with all federal, state, and local laws or regulations presently in existence applicable to the disposal of such waste.

The method of the invention comprises the steps of providing a sealable vessel, providing a highly basic solvent, immersing the waste matter containing the undesirable elements within the solvent within the interior of the vessel, heating the solvent and the waste matter, and allowing the waste matter to remain within the solvent until digested, thereby forming a sterile aqueous solution and sterile solid waste. The extent of digestion or degradation of the waste matter may be increased by treating the waste under pressures above one atmosphere. After cooling, the post-digestion end product may then be directly disposed of through conventional disposal means, such as a sanitary sewer or landfill, or even used as a fertilizing agent in land use applications. If preferred, the post-digestion stage may also include rinsing or flushing of the resultant waste product and the interior of the vessel. The system and method of this invention also substantially reduce the amount of post-digestion solid waste to be disposed of.

The inventors herein have determined that complete digestion (time vs. temperature curves) may be determined by measuring the rate of production of amino acids as the digestion process proceeds. When that process reaches an asymptote, digestion is considered complete.

In operation, when the operator is ready to dispose of the waste matter, such as animal carcasses or remains for example, the waste matter is placed within a holding container that is then placed within the interior of the vessel. The lid of the vessel is then secured by way of conventional lid clamps. The load of waste matter placed in the vessel for digestion should be at least 10% of the capacity of the vessel (by weight) but not more than 40% of the total weight of the capacity of the vessel. The digestion cycle is then initiated, ultimately resulting in the waste matter being completely immersed in the highly basic solvent.

For the purposes of this application, a "highly basic solvent" may include a 1-2 molar (M) aqueous solution of an alkali metal hydroxide or an alkaline earth metal hydroxide. Preferably, this solvent should have a pH of at least above 13, preferably in the range of 13 to 14. An aqueous solution of sodium hydroxide (NaOH—also commonly known as sodium hydrate) or potassium hydroxide (KOH—also commonly known as caustic potash or potassium hydrate) is preferred. While an aqueous solution of NaOH or KOH is preferred, solutions containing calcium oxide (CaO—also commonly known as burnt lime, calx or caustic lime), ammonium hydroxide ($NH_4OH$—also commonly known as aqua ammonia) or magnesium hydroxide are also suitable. An example of a suitable highly basic solvent may consist of a 0.1 M to 2.5 M solution of NaOH in water, or approximately 0.4%-10% sodium hydroxide (by weight) in water.

During digestion, the hydrolyzable material should be immersed in a sufficient amount of solvent such that the material may be digested. One ratio assuring excess base to carry out the digestion of the waste matter to completion, particularly animal tissue, is a 1:10 ratio of alkali metal hydroxide to wet tissue weight. A further expression of this ratio is 40 kilograms of NaOH dissolved in 900 liters of water added to 100 kilograms dry weight protein or 40 kilograms of NaOH in 500 L $H_2O$ added to 500 kilograms fresh or frozen waste matter by weight. These ratios are given only as instruction as to how to conduct the method and operate the system stated herein and not to limit the nature or scope of the invention; one using the system and method described herein may find ratios more economical and exact as the invention is practiced. In order to assure degradation of all infectious wastes, including prokaryotes, the highly basic solvent should be heated to a temperature of at least 100.degree. C., and preferably 110.degree. C. to 150.degree. C.

It is preferable to allow the reaction to proceed in a closed reaction vessel after the waste matter has been immersed within the solvent. Reducing the amount of $CO_2$ available to the reaction is beneficial in order to maintain the ideal rate and stoichiometry of the reaction. This may be done by simply removing or limiting any contact that the highly basic solvent has with the environment.

In the event the reaction between the waste matter such as an animal carcass and the highly basic solvent were allowed to proceed at its natural rate, it may take an impractical amount of time. Therefore, it is advantageous to increase the reaction rate beyond its natural progression. One way to increase the speed of the reaction process is to heat the solvent, preferably to temperatures of 110.degree. C. to 150.degree. C. Conducting the reaction in a sealed vessel under increased atmospheric pressure also reduces the reaction time needed to digest the animal tissue. A preferred mode includes heating the solvent to a temperature of about 150.degree. C. for a duration of about three (3) hours at a pressure of about 2.8 atmospheres. It has been found that the basic rule of thermodynamics or the "Q10 Rule" applies to this invention as well in that for every 10 degrees Celsius rise in temperature, the reaction rate for the chemical reaction taking place within the closed vessel increases two-fold, thereby resulting in the digestion time being reduced by approximately 50%. Such phenomenon is based on the Arrhenius equation. In the present invention, the following minimum digestion times and automated programmed cycle times have been found to be effective at certain predetermined temperatures:

TABLE ONE

| Temperature. ° C. (° F.) | Minimum Digestion Time | Programmed Cycle Time |
|---|---|---|
| 100 (212) | 16 hours | N/A |
| 110 (230) | 8 hours | 16 hours |
| 120 (248) | 4 hours | 12 hours |
| 130 (266) | 2 hours | 8 hours |
| 140 (284) | 1 hour | 5 hours |
| 150 (300). | 5 hour | 3 hours |

Furthermore, detergents to a concentration of up to 1% to the solvent, examples being sodium lauryl sulfate or deoxycholate, may also be added to increase the rate of digestion, if desired. It should also be noted that addition of detergents to the solvent also has the added advantage of dispersing non-saponifiable lipids, and aiding in the sterilization of biological materials.

Ultimately, the reaction rate will depend on specific variables such as: the temperature of the solvent, pressure in the reaction vessel, the nature and volume of the waste matter, i.e., the physical size of the carcasses or waste tissue, and the ratio of waste matter to the volume of the highly basic solvent. As the reaction rate will vary, the time that the waste matter must remain immersed in the solvent will also vary. However, regardless of the reaction rate, the waste matter should remain completely immersed within the solvent until solubilized and hydrolyzed. Allowing the waste matter to remain within the solvent until digestion is achieved will also help produce a more sterile solution.

Once the waste matter such as animal tissue has been digested, two types of solid debris often remain. The first type of debris consists of rubber, plastic, or cellulosic materials that the lab animal may have ingested, as well as debris remaining from experimental or surgical procedures, such as surgical clips, sutures, glass, and bits of plastic or paper. Solid items such as these never incorporate the radioactive isotopes. Once sterilized, such solid items are also not considered biomedical waste in most jurisdictions. This type of debris may often be simply disposed of as ordinary sterile solid waste upon being isolated from the solution and washed.

The second type of solid debris remaining undissolved includes inorganic portions of the animal's skeletal structure and teeth. Unless a radioisotope capable of incorporation into the inorganic portion of bones and teeth is used, the inorganic component of the skeletal remains will not contain the radioactive isotope and may be disposed of as solid sterile waste.

The skeletal remains, when removed from the solvent and washed, are extremely friable.

After the biological waste matter has been digested within the solvent and the solid debris removed, the solution may comprise a diluted concentration of radioactive isotopes that meet the MPC requirements under the federal regulations, as well as an alkaline mixture of alkali metal salts of amino acids and peptides, sugar acids, nucleotides, small peptides, fatty acids from lipids, phosphates from lipid and nucleic acid breakdown, soluble calcium salts, pigments, sugars, sugar alcohols, hydrocarbons, and inorganic acids derived from the electrolytes normally within solution in body fluids. These by-products are identical to those released in vast amounts from cooking leftovers and waste from all commercial and household kitchens. Thus, the solution contains compounds that are non-toxic and are biodegradable by bacteria or fungi found in soil and sewage treatment systems, and possibly a very dilute amount of radioactive solute.

Because the solution at the end of the digestion cycle contains only non-toxic biodegradable materials and the water released from the animal tissue, further dilution of the solution may not be required for safe disposal. Further dilution to reduce the alkalinity of the solution will be accomplished, however, by the rinsing of the vessel and the inorganic remains with excess water, by the temperature regulating co-flush for the effluent, and the general daily effluent volume of the site, institution, or company. (Deliberate dilution of soluble radioactive waste is usually not permitted by the applicable local, state and federal regulations.) At this stage, however, the concentration of radioisotope in the solution should be well within the level that may be safely released to a sanitary sewer.

This sterile, neutral, aqueous solution that contains the breakdown products of cells and tissues, and may contain remnants of radioisotopically labeled solutes may be safely disposed of utilizing methods commonly used to dispose of everyday nontoxic and biodegradable substances. It is entirely safe to dispose of this solution using disposal means such as sanitary sewage systems and other disposal means appropriate for the disposal of these simple biodegradable compounds.

Now turning to FIG. 1, a preferred system 10 for carrying out the invention is shown schematically, comprising a closed reaction chamber or vessel 12 capable of containing the solvent solution and the waste matter such as the animal tissue or carcass or regulated medical waste. A portion of vessel 12 is defined by a double-walled structure for purposes discussed below. Naturally, the vessel must be constructed from material capable of withstanding the pH levels, temperatures, and pressures employed in this invention. One such suitable material is stainless steel. Vessel 12 must also be capable of being closed in an air tight fashion to provide the necessary environment within the vessel interior 14 for the controlled alkaline hydrolysis cycle to be carried out to completion. Thus, the lid or cover 16 of the vessel 12 must be capable of being closed tightly, pressure and air tight, to withstand the temperatures and pressures of the digestion cycle and prevent the inadvertent introduction of atmosphere (particularly carbon dioxide) into the vessel interior or, more importantly, prevent the escape or inadvertent exhausting of the contents of the vessel interior to atmosphere. Such closure of the vessel may be achieved by conventional lid clamps well known in the industry (not shown).

The system and method carried out by this invention are controlled by a conventional programmable logic controller (PLC) means (not shown) defined by a programmable multi-loop machine controller, computerized for automated operation. Such control means preferably includes an information screen, a disk drive for the automation program software, and a keyboard for alternative manual input or operation.

System 10 further includes a weight transducer 18 (shown schematically) coupled to one or more of the legs of the vessel 12 for determining the weight of the waste matter received within the vessel and for generating an output signal indicating such weight data. The transducer is preset such that the weight of the vessel without contents equals zero weight. The contents weight data is then inputted to the PLC control means for, based on the weight output data, determining the appropriate amounts of water and solvent to introduce into the interior of the vessel, utilizing a water supply 20, via conduit 20a, and a spray ball or nozzle 20e located within the vessel interior, and solvent supply 22, via solvent loop conduit 24 and pump 26. Solvent is injected into the interior of vessel 12 via injector means 28, which are shown schematically in FIG. 1 and in more detail in FIGS. 5A through 5D. Injector means 28 mixes and agitates the contents of the vessel interior 14 and enhances the interaction between the highly basic solvent and the waste matter being digested by directing the jet flow of the solvent solution upwardly at the bottom 62 of the container 60 (see FIG. 5A) to keep the vessel contents moving and to prevent waste matter from accumulating at the bottom of container 60 and not mixing thoroughly with the solvent. By doing so, the agitating injector means also shortens the digestion cycle time.

It should be appreciated that this invention is not limited to the agitating injector means described and shown herein but contemplates any means that introduces the solvent into the interior of the vessel. The mere introduction of solvent into the vessel will "mix" the alkali-water solution with the waste matter. Introducing heat also induces mixing. Moreover, agitation of the contents may be achieved by various means, including external mechanisms coupled to the vessel, such as rocking or shaking assembly that physically moves the vessel. All such alternative means of mixing or agitating the vessel contents are contemplated by this invention.

As noted above, the preferred process requires that the solvent solution be heated in order to accelerate the digestion process to completely dissolve the animal tissue, carcasses, or medical waste. To that end, further included in system 10 is a heating means preferably defined by a stainless steel steam jacket 30 arranged circumferentially about the vertical sides and base of vessel 12 for heating the interior of the vessel to a first predetermined temperature level after the introduction of water and solvent into the vessel interior 14. Heated water or steam is circulated between the walls of the double walled vessel 12. While the steam jacket defines a preferred embodiment, any heating means commonly known and used for heating solutions could be utilized in this invention. Steam is supplied to jacket 30 by a steam supply 32 and conduit 32a provided with a cut-off valve 32b and a regulating valve 32c. The system further includes a vent 34, which is disposed in the open state upon initiation of the cycle and thereafter closed by PLC control means when the temperature within the vessel reaches a predetermined first temperature. The temperature within the vessel 12 is gauged by a vessel thermocouple 36a, while the pressure within the vessel is gauged by a PSI transducer 38. The temperature within the solvent loop is gauged by a loop thermocouple 36b.

In the preferred embodiment, an eductor apparatus 40 is utilized for creating a vacuum within the vessel interior 14. When vent 34 is open and flushing water is admitted to the eductor by the water supply 20 via conduit 20b, the action of the eductor draws the air and any odorous gas from within the interior of the vessel through conduit 34a, whereupon the air and odorous gas is eventually entrapped with the flushing water at eductor 40 to, in turn, be removed from the system via drain conduit 42a to sanitary drain 42. The temperature of the fluid at the drain may be gauged by a thermocouple 44 to monitor the effluent temperature prior to disposal in a sanitary sewer system. The vacuum-creating eductor substantially reduces the odorous gases that may escape from rotting carcasses while the vessel is filling, before the vent valve 34 is closed.

In cycle, once the contents of the vessel are drained after the digestion cycle (heating and cooling), the interior of the vessel is rinsed with cold water via sprayball 20e with the drain 41 open. After a few minutes, the drain 41 is closed to allow the vessel to begin to fill with water. Once the vessel is filled to the point where the waste matter is covered, the contents are then agitated by injecting the water solution through injector means 28 for a few minutes to increase the rinsing effect. Drain 41 is then re-opened and the liquid contents of the vessel are allowed to drain. Thereafter, if desired or necessary, the drain 41 is closed for a second time and the vessel is allowed to again fill with water. Heat may then be applied again to the vessel to heat the liquid within the vessel to approximately 105.degree. C. (190.degree. F.), whereupon a reverse ion exchange is initiated. The time and temperature used in this post-digestion heating stage may vary.

To balance or control the vacuum being created within the vessel during the post-digestion cooling cycle and to prevent the vacuum from impeding the draining of the vessel, a vacuum balancing device 46 shown and discussed below in relation to FIGS. 4A-4C is provided that selectively admits ambient air to the vessel interior when the internal vacuum pressure reaches or exceeds the threshold pressure of the vacuum balancer 46. While the vacuum balancer shown and discussed herein is of a unique design, any vacuum balancing device that will not leak fluid or collect condensed fluid may be suitable for the effective operation of this invention.

Referring now to FIG. 4A, vacuum balancer 46 is shown in detail comprising a vacuum clamp 47, a vacuum plug 48, an annular end cap 49, a vacuum gasket 50, an O-ring 51, a flat washer 52, a socket head cap screw 53, an upper ferrule portion 54, a lower ferrule portion 55, a spring 56 and a thermometer cap 57. In its closed state as shown in FIG. 4C, spring 56 urges the cap screw 53, washer 52 and the vacuum plug 48 upwardly such that O-ring 51 abuttingly engages the vacuum gasket 50, thereby preventing any air from passing therethrough. When the internal vacuum pressure within vessel 12 reaches a certain point, it will overcome the force of the spring 56, thereby allowing the plug 48 to move downwardly causing O-ring 51 to disengage from the gasket 50, as shown in FIG. 4B, to admit ambient air into the vessel interior while the eductor 40 draws air out of the vessel interior.

The preferred system further includes a permeable container capable of holding the waste tissue or remains or medical waste within the vessel interior 14 during the digestion cycle to completely immerse the waste tissue within the solvent solution. As shown in FIGS. 3A-3C, such a container preferably includes a cylindrical article 60 defined by a steel mesh screen 62 having an upper rim portion 64, a lower rim portion 66, and a lid 68 to enclose the waste tissue within the container 60. (While the preferred shape of the container is cylindrical, other non-cylindrical shapes are suitable and should be considered as being within the scope of this invention.) Attached to the lid 68 is preferably a handle 68a. As shown in FIGS. 3B and 3C, both the lid 68 and the bottom of the container include the stainless steel mesh 62, which is preferably constructed from stainless steel screen mesh having one-eighth (⅛) to one-quarter (¼) inch screen mesh. The lid 68 may be releasably secured to the body 61 of the container via conventional means. Handle 68a may be equipped with an eyelet-like portion 68b to receive attachment means for lowering and raising the container into and out of the vessel interior. When the waste tissue is digested, the permeable container 60 may be hoisted out of the vessel 12, or removed out of another port arranged in the side of the vessel 12 during a "clean side" removal as discussed below, thereby removing the undigested solid debris remaining within the container 60. The height "h" (FIG. 3A) and diameter "d" (FIG. 3C) of the container may be varied to accommodate varying amounts of waste tissue or carcasses or animals of varying sizes, or of medical waste of varying volume or quantity. For the larger containers, it may be necessary to employ a mechanical hoist system to lower the heavier or more voluminous loads of carcasses of larger animals or larger quantities of medical waste into the vessel interior.

As noted above, the preferred embodiment includes agitating injector means 28 shown in FIGS. 5A-5D to accelerate the reaction rate between the solvent solution and the waste tissue by keeping the solvent in motion while the reaction is occurring. One such means is accomplished by circulating the solvent via loop 24 and pump 26 (FIG. 1) and introducing the solvent into the interior of the vessel by injecting it via multiple jet ports at varying angles generally aimed at the bottom of the holding container 60 (see FIG. 5A). Such an arrangement keeps the solvent moving within the vessel interior, as well as keeping waste matter from accumulating on the bottom of the container 60, which can result in the prolonging or slowing of the digestion process. Agitating injector means 28 preferably comprise a plurality of concentric flow reducers or nozzles 28a coupled to a respective elbow members 28b, which in turn are coupled to respective tube members 28c, which finally are coupled to respective cross member 28ds. Each cross member 28d is connected to a screw-coupling member 28e for affixing the injector means to the upper end of the inflow conduit 24a. In a preferred embodiment, the opposing nozzles 29a are disposed at an included angle A of about 22.5 degrees (FIG. 5C), while opposing nozzles 29b are disposed at an included angle B of about 45 degrees (FIG. 5D), to enhance the agitation and mixing action of the injectors to facilitate the digestion reaction.

Figure 5A:
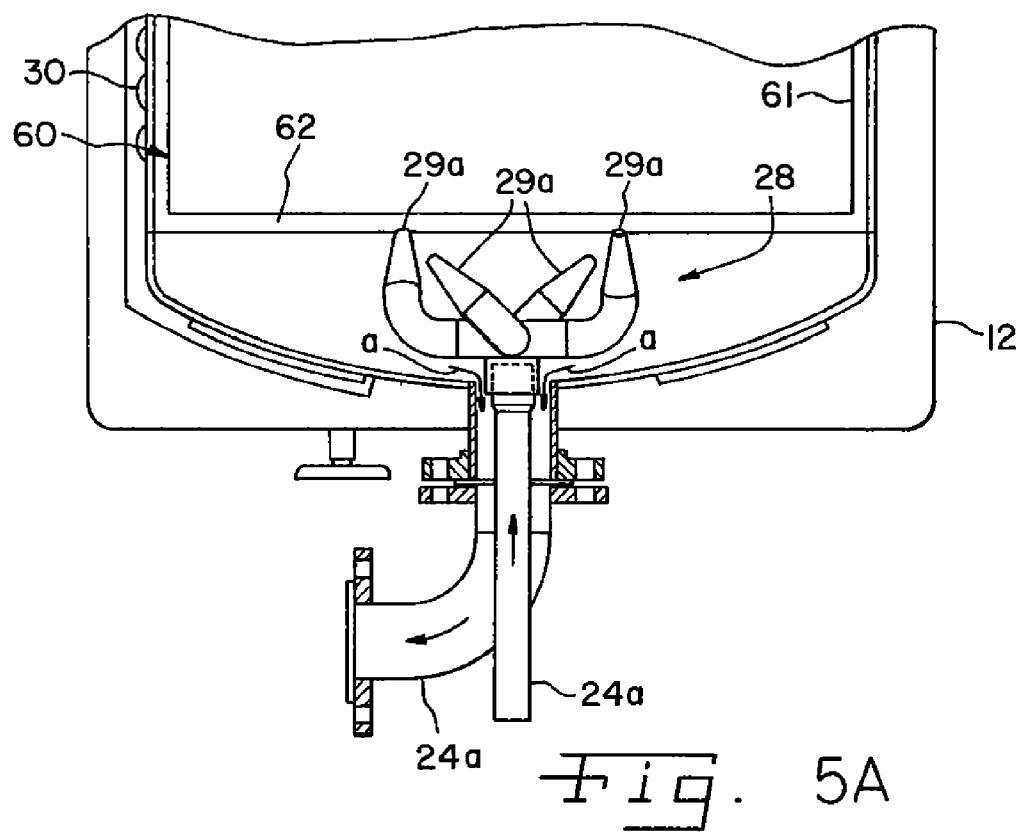
FIGS. 5A-5D show various views of agitating injector means provided by this invention.
Figure 5B:
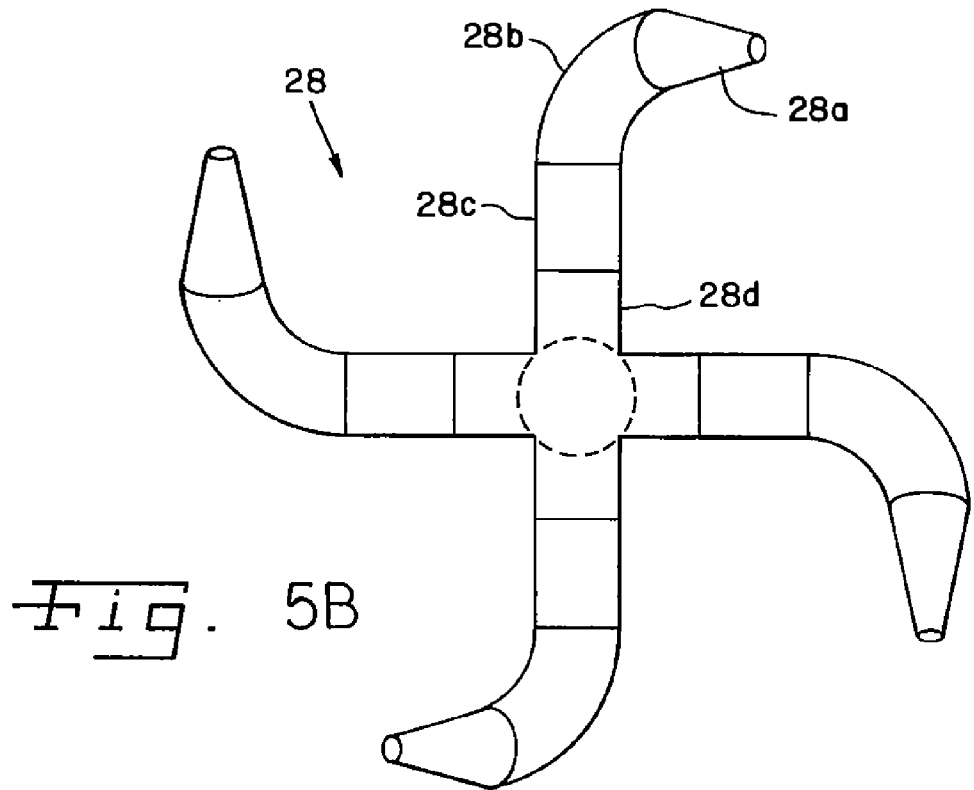
Figure 5C:
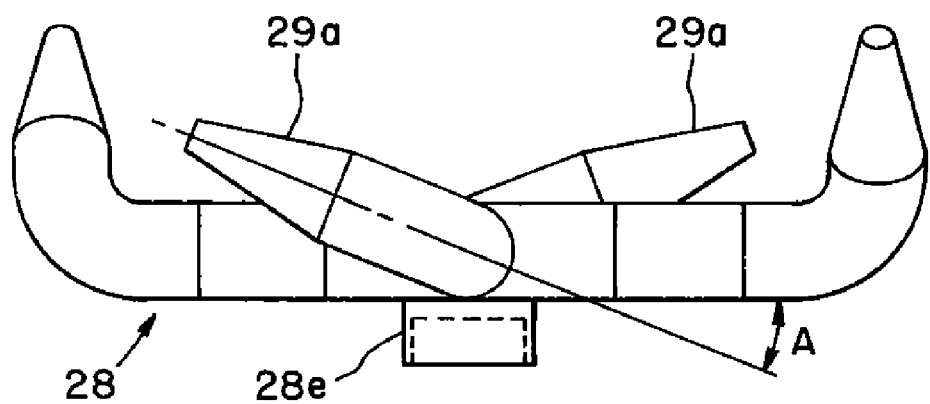
Figure 5D:
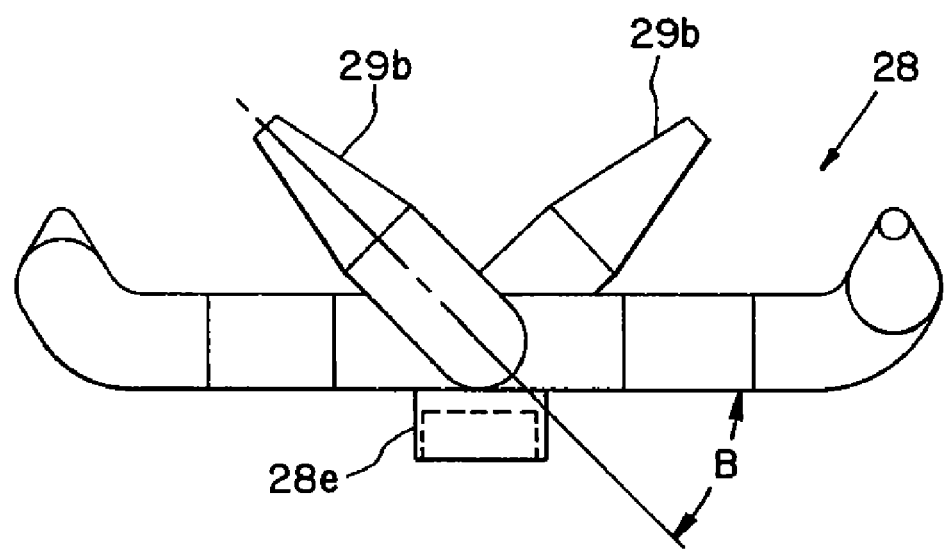

As shown in FIG. 5A, the inflow conduit 24a delivering solvent to injector 28 extends into and, in a coaxial fashion, extends upwardly through the outflow conduit 24b. Inflow conduit 24a is smaller in diameter than outflow conduit 24b such that the aqueous interior contents of the vessel 12 may drain downwardly into outflow conduit 24b as shown by the reference arrows "a" in FIG. 5A. Outflow conduit 24b carries the solvent back to the solvent loop 24 and pump 26 (see FIG. 1) and when necessary, through drain valve 41 to the sanitary drain 42. It will be understood by those skilled in the art that the points of connection "b" shown in FIG. 5A must be sufficiently tight and withstand the highly basic, high-temperature, and high-pressure environment. It should be further understood the injector means may include separate injector nozzles disposed in fixed arrangements about the interior of the vessel to direct solvent at the waste matter. Such a configuration is useful in larger applications involving large diameter containers and large-volume waste matter. Such separate fixed injections may be utilized in lieu of or in addition to the injector assembly 28 shown and described herein.

Figure 2:
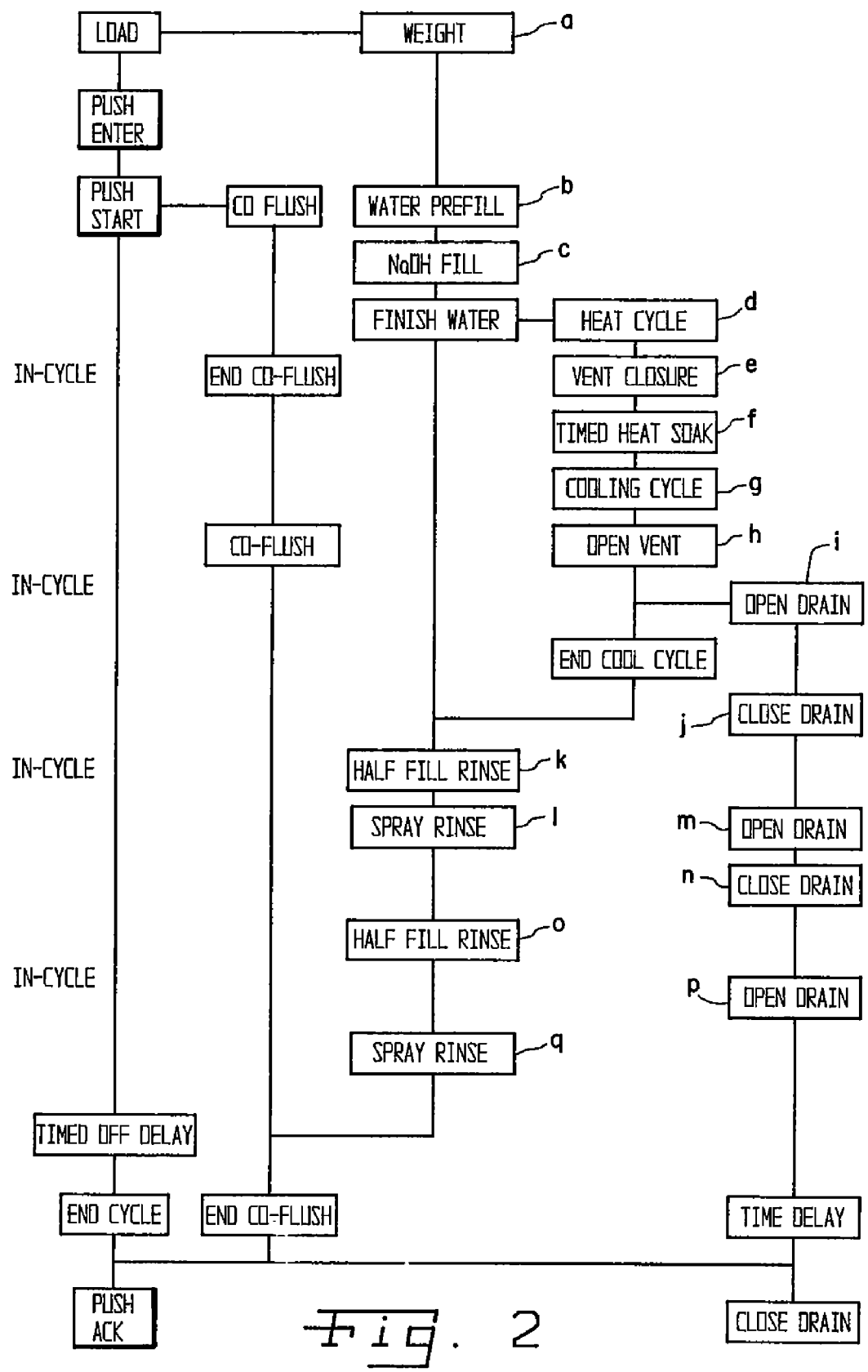
FIG. 2 is a flowchart representation of the method provided by a currently preferred embodiment of the invention.

FIG. 2 presents a flowchart depicting the cycle process of this invention. In operation, the waste matter is weighed and the weight and water and solvent ratios automatically determined by the PLC control means (box a). The appropriate amount of water (box b) and solvent (box c) is then introduced into the interior of the vessel based on the weight calculations made by the PLC control means. Water is added at the rate of 60% water to 40% tissue by weight. The alkali is added at the predetermined concentration based on the tissue weight. This is typically equivalent to a solution of 50% NaOH added by weight at a ratio of 15 to 20% of the total tissue weight. The heating means 30 (FIG. 1) then heats the vessel interior (box d) to the digestion cycle temperature while closing the vent 34 (box e). System 10 then maintains that elevated temperature for a predetermined duration (box f) as calculated by the PLC control means based on the weight of the waste matter placed in the vessel for digestion. The system typically maintains the digestion temperature at about 150.degree. C. (302.degree. F.) for about 3 hours, or if operated at a lower temperature, for a time at least double the digestion time for that temperature (doubling the minimum digestion time for each 10 degrees Celsius decrease in temperature) in accordance with the thermodynamics equation discussed above.

Next, the system goes into the cooling cycle after digestion whereupon cooling water is admitted to the steam jacket interior 30 from water supply 20 (FIG. 1) via conduit 20*c* to lower the temperature of the vessel interior (box g). This continues until the internal pressure within the vessel reaches about atmospheric pressure (101.3 kilopascals/14.7 pounds per square inch (PSI)), shown as a reading of zero on the pressure gauge or transducer, which measures pressure above 1.0 atmosphere. Once the system is cooled sufficiently, the vessel is drained to the sewer (sanitary drain 42) by the control means opening the vent 34 (box h) and drain 41 (box i) to drain the liquid contents from within the vessel interior down to a predetermined point, at which point drain 41 is closed (box j) while flushing water is continued to be introduced to flush the vessel interior (box k) until the interior is preferably about half full. At that point in the cycle, the vessel interior is sprayed with rinsing liquid and the contents are circulated through the injectors 28 for a predetermined time before the drain is again opened to rinse away any residual materials remaining within the interior of the vessel (boxes l and m). The drain is then closed again (box n) and the vessel partially filled again and a final heated rinse cycle is then carried out (boxes o, p, and q). At this stage, the digestion and cooling cycle are complete and the vessel may be opened and the waste holding container removed and emptied. The empty container is then replaced within the vessel interior rendering the system ready for subsequent operation.

This invention also presents a method for digesting or neutralizing waste matter comprising organic tissue or infectious, biohazardous, hazardous, or radioactive agents, by subjecting the waste matter to a controlled alkaline hydrolysis cycle and generating a sterile resultant suitable for conventional sanitary disposal. The preferred method compromises the steps of:

(a) providing a closed reaction vessel 12 coupled to a heating-cooling means;

(b) receiving the waste matter within the closed reaction vessel (c) determining the weight of the waste matter received within said vessel and generating weight output data by way of a weight transducer 18 coupled to the vessel 12;

(d) controlling the operation of the system, including receiving and considering the weight output data generated by the weight determining transducer 18 and determining the appropriate amounts of water and solvent to introduce into the interior of the vessel 12;

(e) after determining the appropriate amounts of water and solvent to introduce into the interior of the vessel, initiating a vacuum on the vent of the vessel to remove odors while introducing water within the vessel interior in an amount determined by the PLC controller via water supply 20 and conduit 20*a* based on the weight output data, and introducing the highly basic solvent into the interior of the vessel in an amount determined by the PLC controller based on the weight output data;

(f) heating the interior of the vessel to a first predetermined temperature level by way of the heating means (steam jacket 30) after the introduction of water and alkali solution into the interior of the vessel;

(g) mixing or agitating the contents of the vessel to enhance the interaction between the solvent and the tissue by way of agitating injector means 28;

(h) continuing to vent the interior of the vessel by way of vent 34 upon initiation of the digestion cycle and closing the vent when the temperature within the vessel reaches a first predetermined temperature;

(i) heating the vessel interior to the digestion cycle temperature and maintaining that temperature for a predetermined duration;

(j) cooling the interior of the vessel after the digestion cycle has run by introducing cooling water from supply 20 to heating means 30;

(k) operating eductor 40 and opening vent 34, thereby creating a vacuum, to remove any odorous gases from within the vessel throughout the remainder of the post-digestion process;

(l) balancing the vacuum created by eductor 40, via vacuum balancer 46, to prevent such vacuum from interfering with the draining of the vessel by selectively admitting ambient air into the vessel interior during the remainder of the post-digestion process;

(m) opening drain 41 to drain the digested liquid portion of the vessel contents and initiating a spray rinse by opening line 20*a* to remove any remnants of the solvent solution from the solid waste remains within the vessel interior;

(n) closing drain 41 while maintaining spray line 20*a* open to continue the spray rinse via sprayball 20*e*, and opening water line 20*d* to refill the vessel with water to approximately 15.24 cm (6 in.) above the bottom of the digestion container 60 and restarting the pump 26 to recirculate the rinse solution throughout the solid waste remains via loop 24 for a predetermined time to allow for additional rinsing of the solid waste remains;

(o) opening drain 41 to drain the rinsing liquid portion of the vessel contents;

(p) initiating another spray rinse by opening line 20*a* to further remove any remaining solvent rinse solution from the solid remains;

(q) closing drain 41 while maintaining spray line 20*a* open and opening water line 20*d* to, again, refill the vessel with water to approximately 15.24 cm (6 in.) above the bottom of the digestion container 60 and restarting the pump 26 to recirculate a rinse solution throughout the solid waste remains for a second time;

(r) heating the second rinse solution to a predetermined temperature and recirculating the second heated rinse solution for a predetermined time to allow the solution to remove any entrained digestion solution from the solid waste remains;

(s) opening drain 41 to allow the second heated rinsing solution to drain;

(t) opening spray line 20*a* for a final rinse of the vessel interior and solid waste remains while maintaining drain 41 open; and (u) closing spray line 20a to discontinue the rinse and allowing the liquid contents of the vessel to drain; and (v) finally, opening the lid 16 of the vessel and removing the waste remains from the primary opening for disposal in a sanitary landfill or for usage as solid fertilizer material.

As mentioned above, an additional feature of the closed vessel is to allow the solid waste remains to be removed from a secondary opening (not shown) arranged on the vertical side of the vessel. This feature allows the vessel to be positioned in such a configuration that the primary opening may be located within a contaminated portion of the facility, while the remaining portions of the system are located within a clean portion of the facility. This would allow contaminated materials to be processed and sterilized, then for the sterile solid waste remains to be removed from the secondary opening as sterile remains into a clean area for final disposal. Thereafter, the secondary opening would be sealed prior to the opening of the primary opening for the loading of waste for another processing cycle. Such a configuration is referred to as "dirty side feed/clean side removal." Such an embodiment would alter step (u) above to read as follows:

(u) finally, opening the vessel and removing the solid waste remains from the secondary opening for disposal in a sanitary landfill or for usage as solid fertilizer material, then closing and re-sealing the secondary opening prior to opening the primary opening for the loading of new waste material for a subsequent cycle, wherein the dirty side door or lid and the clean side door or lid are electrically interlocked to assure compliance with regulations and prevent contamination of the clean side.

Finally, set forth below is an example of the system of this invention and its method of operation in use.

Example One

Prior to filling the vessel with, for example, animal carcasses containing infectious or hazardous agents, the lid of the vessel is closed in order to "zero" the load scale. The lid is then opened and the vessel filled with waste matter to the desired volume. Preferably, the load should be at least 20% of the vessel's capacity (by weight) but not more than the weight capacity of the vessel, in which case the system will not operate and the excess weight must be removed. The vessel lid is then closed and secured. The PLC controller is then activated to initiate the digestion process by first determining the weight of the waste matter within the vessel. The digestion cycle is then initiated whereby waste is preferably added at the rate of 60% waste to 40% tissue by weight, alkali is added at the predetermined concentration based on the tissue weight. Such concentration is normally equivalent to a solution of 50% HaOH added by weight at a ratio of 15 to 20% of the total tissue weight.

The heating step is then initiated to raise the temperature of the interior of the vessel to the predetermined first digestive cycle temperature for a predetermined duration to completely digest the carcasses. In a preferred mode, the cycle holds the digestion temperature to at least 110.degree. C., preferably about 130.degree. C., and most preferred about 150.degree. C. At 150.degree. C., the digestion cycle is normally about 3 hours in duration.

Once the digestive cycle is complete, the PLC control means initiates the cooling cycle, utilizing cold water flushed through the sleeve jacket 30 of the vessel. Once the vessel has cooled sufficiently, the vessel is drained to the sewer, then partially refilled with cold water and the interior rinsed. The vessel is then drained again, partially refilled again and this second rinse solution heated if desired. After this hot rinse, the vessel is then drained and it contents sprayed with a final spray rinse. The cooling cycle is then complete and the system shuts down while the drain is opened to empty completely the interior of the vessel.

If the operator is present at the completion of the cooling cycle, the vessel may at that point be opened and the waste-carrying basket removed and emptied. The basket is then replaced, making the system ready for a new cycle. In the event, however, the operator is not present when the cooling cycle is complete, when the cycle runs at night for example, the operator should initiate the rinse cycle for a short duration, preferably about 30 seconds. After the final spray is complete, the vessel may be opened and the waste safely disposed of.

Although the invention has been described with a preferred embodiment, those skilled in the art will understand that modifications and variations may be made without departing from the scope of the inventions as set forth in the following claims. Such modifications and variations are considered to be within the purview and scope of the appended claims.

The invention claimed is:

1. A method for digesting or neutralizing biologically active waste matter, said waste matter including hazardous or biohazardous agents or regulated medical waste containing infectious agents, said infectious agents comprising hydrolyzable material, said method comprising the steps of:
   (a) providing a highly alkaline solvent;
   (b) immersing said biologically active waste matter into said highly alkaline solvent; and
   (c) heating said highly alkaline solvent and said immersed biologically active waste matter to a temperature of at least 110° C. and at a pressure greater than about 2.8 atmospheres and for a time sufficient to digest said hydrolyzable material, whereby a sterile solution comprising non-toxic biodegradable materials and containing sterile solid waste free of said infectious agents is produced.

2. The method of claim 1 wherein said highly alkaline solvent has a pH in the range of about 13 to about 14.

3. The method of claim 1 wherein said highly alkaline solvent comprises a mixture of water and an alkali metal hydroxide or alkaline earth-metal hydroxide.

4. The method of claim 1 wherein said heating step (c) is performed at a temperature of at least 130° C.

5. The method of claim 1 wherein said heating step (c) is performed at a temperature of about 150° C.

6. The method of claim 1 further comprising agitating, circulating, or stirring the highly alkaline solvent in step (c).

7. A method for digesting or neutralizing infectious waste matter, said infectious waste matter including hazardous or biohazardous agents or regulated medical waste containing infectious agents, said infectious agents comprising hydrolyzable material, said method comprising the steps of:
   (a) providing a highly alkaline solvent;
   (b) immersing said infectious waste matter into said highly alkaline solvent; and
   (c) heating said highly alkaline solvent and said immersed infectious waste matter to a temperature of at least 130° C. and for a time sufficient to digest said hydrolyzable material, whereby a sterile solution comprising non-toxic biodegradable materials and containing sterile solid waste free of said infectious agents is produced.

8. The method of claim 7 wherein said heating step (c) is performed at a pressure of at least about 2.8 atmospheres.

9. A method for digesting or neutralizing biologically infectious materials such as organic tissue or hazardous or biohazardous agents or regulated medical waste by subjecting them to an alkaline hydrolysis cycle and generating a sterile resultant suitable for conventional sanitary disposal or land application, said method compromising the steps of:
(a) providing a closed reaction vessel coupled to a heating-cooling means;
(b) receiving the biologically infectious materials within said vessel;
(c) determining the weight of the biologically infectious materials received within said vessel and generating weight output data;
(d) controlling the operation of the system, including considering the weight output data and determining the appropriate amounts of water and alkaline compound to introduce into the interior of the vessel;
(e) after step (d), introducing an alkaline compound within the interior of said vessel in an amount based on the weight output data;
(f) after step (d), introducing water within the interior of said vessel in an amount based on the weight output data; and
(g) after steps (e) and (f), heating the vessel interior to a first temperature for a sufficient duration to produce a safely disposable resultant.

10. The method of claim 9 wherein said highly alkaline solvent has a pH of at least about 13.

11. The method of claim 9 wherein said highly alkaline solvent comprises a mixture of water and an alkali metal hydroxide or alkaline earth-metal hydroxide.

12. The method of claim 9 wherein said heating step (h) is performed at a temperature of at least 110° C.

13. The method of claim 9 wherein said heating step (h) is performed at a temperature of at least 130° C.

14. The method of claim 9 wherein said heating step (h) is performed at a temperature of about 150° C.

15. The method of claim 9 wherein said heating step (h) is performed at a pressure of at least about 2.8 atmospheres.

16. The method of claim 7, further comprising the steps of: (d) cooling the sterile solution to a predetermined temperature; and (e) decreasing the pressure to about atmospheric pressure.

17. The method of claim 7, wherein the highly alkaline solvent has a pH in the range of about 13 to about 14.

18. The method of claim 7, further comprising agitating, circulating, or stirring the highly alkaline solvent in step (c).

* * * * *